(12) United States Patent
Schöne et al.

(10) Patent No.: US 9,241,795 B2
(45) Date of Patent: Jan. 26, 2016

(54) PROCESS FOR PREPARING CERAMIC IMPLANTS FOR MEDICAL PURPOSES

(75) Inventors: Andre Schöne, Bad Säckingen (DE); Jens Fischer, Bad Säckingen (DE); Karsten Schröder, Bad Säckingen (DE); Hartmut Steffen, Bad Säckingen (DE); Wilfried Besch, Greifswald (DE); Andreas Vogelsang, Hamburg (DE); Klaus-Dieter Weltmann, Ostseebad Binz (DE); Barbara Nebe, Rostock (DE); Steffi Schroder, legal representative, Greifswald (DE); Beatrix Fett, legal representative, Greifswald (DE)

(73) Assignee: VITA ZAHNFABRIK H. RAUTER GMBH & CO., Bad Sackinghen (DE)

( * ) Notice: Subject to any disclaimer, the term of this patent is extended or adjusted under 35 U.S.C. 154(b) by 66 days.

(21) Appl. No.: 14/236,740

(22) PCT Filed: Sep. 5, 2012

(86) PCT No.: PCT/EP2012/067286
§ 371 (c)(1),
(2), (4) Date: Apr. 3, 2014

(87) PCT Pub. No.: WO2013/034583
PCT Pub. Date: Mar. 14, 2013

(65) Prior Publication Data
US 2014/0214174 A1    Jul. 31, 2014

Related U.S. Application Data

(60) Provisional application No. 61/531,386, filed on Sep. 6, 2011.

(30) Foreign Application Priority Data

Sep. 6, 2011  (EP) .................................... 11180268

(51) Int. Cl.
| | | |
|---|---|---|
| A61F 2/28 | (2006.01) |
| B05D 1/02 | (2006.01) |
| A61K 6/02 | (2006.01) |
| C04B 41/83 | (2006.01) |
| C04B 41/00 | (2006.01) |
| C04B 41/48 | (2006.01) |
| A61L 27/10 | (2006.01) |
| A61L 31/02 | (2006.01) |
| C04B 111/00 | (2006.01) |

(52) U.S. Cl.
CPC ................. *A61F 2/28* (2013.01); *A61K 6/0205* (2013.01); *A61L 27/10* (2013.01); *A61L 31/026* (2013.01); *C04B 41/009* (2013.01); *C04B 41/48* (2013.01); *C04B 41/83* (2013.01); *A61L 2400/18* (2013.01); *A61L 2430/02* (2013.01); *A61L 2430/12* (2013.01); *C04B 2111/00836* (2013.01)

(58) Field of Classification Search
CPC ................. A61F 2/28; A61F 2/38; B05D 1/02
See application file for complete search history.

(56) References Cited

U.S. PATENT DOCUMENTS

| | | | |
|---|---|---|---|
| 4,757,014 | A | 7/1988 | Hendrickson et al. |
| 8,257,606 | B2 | 9/2012 | Stephan et al. |
| 2003/0019843 | A1 | 1/2003 | Kawai et al. |
| 2005/0106534 | A1 | 5/2005 | Gahlert |
| 2009/0176191 | A1 | 7/2009 | Gahlert |
| 2011/0053113 | A1 | 3/2011 | Schnabelrauch et al. |

FOREIGN PATENT DOCUMENTS

| | | |
|---|---|---|
| CH | 702731 A1 | 8/2011 |
| CN | 102089016 A | 6/2011 |
| GB | 2407523 A | 5/2005 |
| WO | 0185635 A1 | 8/2001 |
| WO | 2007019323 A2 | 2/2007 |
| WO | 2009103775 A2 | 8/2009 |

OTHER PUBLICATIONS

Finke et al., "Positively Charged Plasma Polymerized Titanium Boosts Osteoblastic Focal Contact Formation in the Initial Adhesion Phase," Biomaterials 28:4521-4534 (2007).

untreated ceramic surface

PPAAm treated ceramic surface ceramic surface with low roughness

Puleo et al., "A Technique to Immobilize Bioactive Proteins, Including Bone Morphogenetic Protein-4 (BMP-4) on Titanium Alloy," Biomaterials, 23(9):2079-87 (2002).

Siow et al., "Plasma Methods for the Generation of Chemically Reactive Surfaces for Biomolecule Immobilization and Cell Colonization—A Review," Plasma Processes and Polymers, 3(6-7):392-418 (2006).

*Primary Examiner* — Jason-Dennis Stewart

(74) *Attorney, Agent, or Firm* — Dardi & Herbert, PLLC.; Curtis B. Herbert

(57) ABSTRACT

A process for manufacturing a ceramic implant with a surface which forms a permanent bonding to bone cell tissues, the surface providing improved osseointegration, the process comprising the step of:—a pretreatment of the ceramic material with the surface wherein said surface of the ceramic material is exposed to a conditioning plasma, which is produced by means of direct current (DC) or alternating current (AC), such as high or radio frequency (HF, RF), or microwaves (MW) at a low pressure, followed by a second step;—a treatment with a reactive plasma in which an organic compound is added to the plasma for the at least partial application of an organic phase to said surface wherein the organic compound is selected from the group consisting of aliphatic amines, cyclic amines, unsaturated and aromatic amines as well as combinations thereof.

11 Claims, 4 Drawing Sheets untreated ceramic surface
PPAAm treated ceramic surface
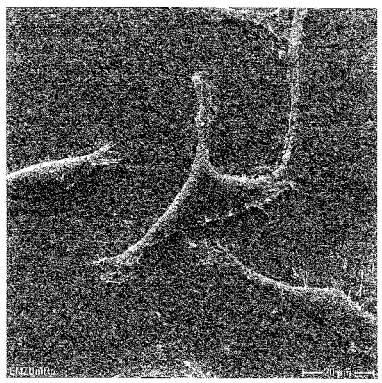
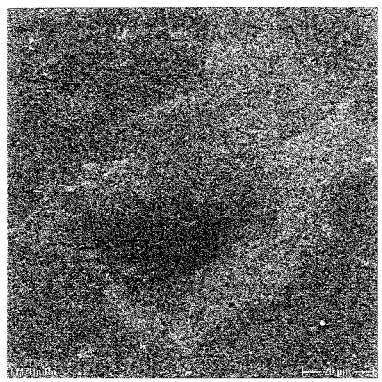
ceramic surface with low roughness
Fig. 2A
Fig. 2B
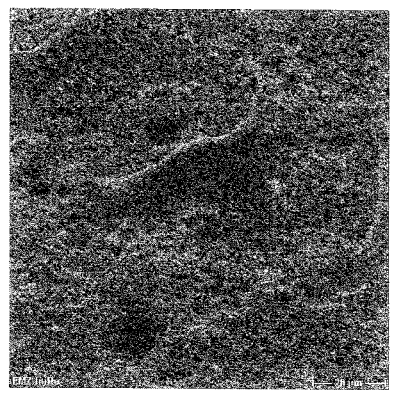
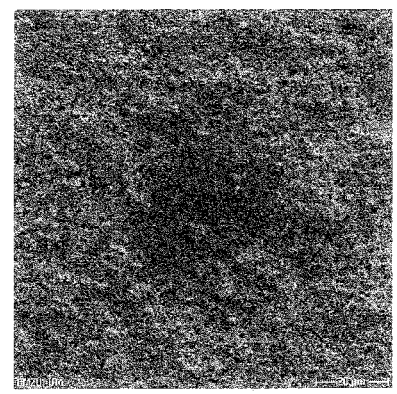
ceramic surface with high roughness
Fig. 2C
Fig. 2D untreated ceramic surface ceramic surface with low roughness ceramic surface treated with 120s Ar/O$_2$-atmospheric pressure plasma ceramic surface with high roughness

PROCESS FOR PREPARING CERAMIC IMPLANTS FOR MEDICAL PURPOSES

CROSS-REFERENCE TO RELATED APPLICATIONS

This Application is a national stage filing of PCT Application Number PCT/EP2012/067286 filed Sep. 5, 2012, which claims priority to EP 11180268.2 filed Sep. 6, 2011 and to U.S. Provisional Application No. 61/531,386 filed Sep. 6, 2011, each of which are hereby incorporated by reference herein.

TECHNICAL FIELD

The present invention is related to a preparation process of ceramic implants for medical purposes having a surface that forms a permanent bond to cell tissues, especially bone cells, to an implant obtainable by the process according to the invention, and to the use of the implant according to the invention.

BACKGROUND

The design of ceramic surfaces in implants, especially dental implants, is still in its beginnings in contrast to metallic implants. Commercially available products are mostly roughened by sandblasting and ensure thus a better mechanical anchoring in the cell tissue in comparison to smooth surfaces. However, they require relatively long times for osseointegration compared to the highly developed surfaces of titanium implants. Thus, in combination with one-part ceramic implants as usual today, there is an additional risk in the osseointegration of these implants.

Introduction

The sandblasted surface is non-optimal for the interface between the ceramic and the surrounding bone.

This disadvantage could be eliminated by the wet-chemical application of polymers such as polyallylamine or proteins or matrix molecules, such as collagens, fibronectin or osteonectin. However, these tend to adhere poorly to the exposed surfaces of the implants, and an early interface fracture may occur. When cell-side stimulants (e.g., BMPs or interleukins) are employed, the products cannot be sterilized because of the thermolability of the proteins, and thus are hardly suitable for clinical use in implantology.

US-A-2009/01766191 discloses the coating of ceramic surfaces with a thin titanium film. However, no information is given about the durability of the adhesion of this layer, and the advantage of metal-free ceramics as an implant material is thwarted.

WO-A-2001/1019323 describes a coating process of Mg-stabilized zirconia ceramic, which is unsuitable for bone contact. Moreover, the ceramic must have a roughness of less than 10 nm as a precondition.

U.S. Pat. No. 4,757,014 discloses a plasma treatment of plastics in order to apply thereto first a layer of a polymer or a silane-functionalized compound for protein immobilization, and thereafter a biologically active protein. The plasma treatment is carried out with a radiofrequency plasma (10-125 kHz) at 10 mTorr to 10 Torr (low pressure to atmospheric pressure) in air, oxygen, carbon dioxide, argon, helium, nitrogen oxides or water vapor to produce functional groups for the immobilization of biologically active proteins and enzymes.

Coatings on the ceramic as described in GB-A-2 407 523 do not solve the problem of an improved contact formation between cells and the grafted implant sufficiently either. In this patent, ceramic-like coatings are applied by means of plasma spraying, vacuum plasma spraying, air plasma spraying or high-velocity oxygen fuel (HVOF) coating.

WO 01/85635 A discloses a method of coating the surface of an inorganic substrate of glass, silicon dioxide, ceramics or carbon, which method includes a step of cleaning the surface of the substrate by subjecting the surface to a reducing gas plasma, a step of activating the surface by generating radicals on the surface of the substrate by subjecting the surface to a reducing gas plasma and forming a first layer on the substrate surface using a plasma enhanced polymerization process employing one or more monomers comprising monomers with a sufficient low molecular weight for them to be in their gaseous state in the gas plasma, selected from the group consisting of $C_1$-$C_{16}$ alkanes, $C_2$-$C_{16}$ alkenes, $C_2$-$C_{16}$ alkynes, styrene, aromatic monomers of styrene compounds, monomers of vinyl- and acrylate-compounds.

WO 2009/103775 A discloses a method for the coating of a surface of a ceramic basic body with a titanium compound, comprising the steps of (i) providing a preformed ceramic material; (ii) at least one step of surface activation of said ceramic material using a plasma for plasma-chemical surface preparation wherein the plasma comprises high-energy ions; (iii) at least one step of applying a titanium compound bonding layer to said ceramic material by plasma-supported coating wherein the plasma-supported coating is performed in pulsed and/or non-pulsed version; (iv) at least one step of applying a functional titanium compound layer by pulsed plasma-supported coating.

CH 702 731 A is related with fabricating a part comprising a substrate and an elastomeric coating, comprises: (a) optionally, treating the substrate to generate active groups on surface; (b) applying to the substrate a first composition comprising at least a first elastomeric material, at least one silane and optionally at least one bonding agent to form an intermediate layer; (c) applying a second composition comprising a second elastomeric material to form the coating; and (d) annealing the formed part.

The production of chemically reactive surfaces with plasma polymers [K. S. Siow, L. Britcher, S. Kumar, H. J. Griesser, Plasma Process. Polym. 3 (2006), 392-418] is substantially more suitable. This review mainly describes radiofrequency (RF) excited plasmas (10 kHz to 1 MHz) in the low-pressure region for producing coatings having a thickness of 50-500 nm. Alternatively, microwave plasmas (1 MHz to 20 GHz) may also be used for this purpose [Finke, B.; Lüthen, F.; Schröder, K.; Mueller, P. D.; Bergemann, C.; Frant, M.; Ohl, A.; Nebe, J. B. Positively charged plasma polymerized titanium boosts osteoblastic focal contact formation in the initial adhesion phase, Biomaterials 28 (2007), 4521-4534].

Puleo D A et al report in Biomaterials 2002 May; 23(9): 2079-87 that immobilization of biomolecules on surfaces enables both localization and retention of molecules at the cell-biomaterial interface. Since metallic biomaterials used for orthopedic and dental implants possess a paucity of reactive functional groups, biomolecular modification of these materials is challenging. In the present work, they investigated the use of a plasma surface modification strategy to enable immobilization of bioactive molecules on a "bioinert" metal. Conditions during plasma polymerization of allylamine on Ti—6Al—4V were varied to yield 5 ("low")- and 12 ("high")-$NH_2$-groups/$nm^2$. One- and two-step carbodiimide schemes were used to immobilize lysozyme, a model biomolecule, and bone morphogenetic protein-4 (BMP-4) on the aminated surfaces. Both schemes could be varied to control the amount of protein bound, but the one-step method destroyed the activity of immobilized lysozyme because of crosslinking. BMP-4 was then immobilized using the two-step scheme. Although BMP bound to both low- and high-$NH_2$ surfaces was initially able to induce alkaline phosphatase activity in pluripotent C3H10T1/2 cells, only high amino group surfaces were effective following removal of weakly bound protein by incubation in cell culture medium.

However, the adhesion of thus prepared coatings on titanium is rather poor. Ceramic surfaces have a similar behavior. The adhesion forces are further reduced because of the high mechanical material differences between the ceramic substrate and the polymer-like coating, which results in a more reduced layer adhesion.

BRIEF DESCRIPTION OF THE FIGURES

FIG. 2A is a scanning electron micrograph image of an untreated ceramic surface having low roughness;

FIG. 2B is a scanning electron micrograph image of a treated ceramic surface having low roughness;

FIG. 2C is a scanning electron micrograph image of an untreated ceramic surface having high roughness;

FIG. 2D is a scanning electron micrograph image of an treated ceramic surface having high roughness;

DETAILED DESCRIPTION

Figures 1A, 1B:
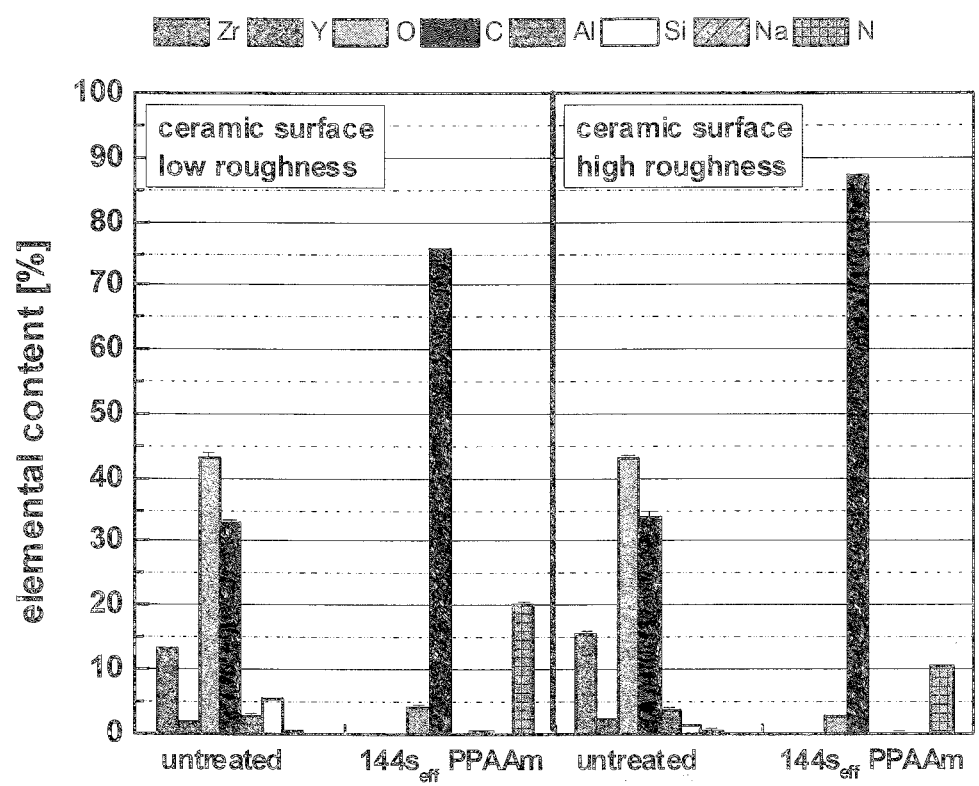
FIG. 1A is a plot of an XPS surface analysis of a ceramic surface having a low roughness.
FIG. 1B is a plot of an XPS surface analysis of a ceramic surface having a high roughness.

An object of the present invention is to provide a process for preparing an implant that ensures improved healing and osseointegration.

The object of the present invention is achieved by a process for manufacturing a ceramic implant with a surface which forms a permanent bonding to bone cell tissues, the surface providing improved osseointegration, the process comprising the step of
   a pretreatment of the ceramic material with the surface wherein said surface of the ceramic material is exposed to a conditioning plasma, which is produced by means of direct current (DC) or alternating current (AC), such as high or radio frequency (HF, RF), or microwaves (MW) at a low pressure, followed by a second step which is
   a treatment with a reactive plasma in which an organic compound is added to the plasma for the at least partial application of an organic phase to said surface wherein the organic compound is selected from the group consisting of aliphatic amines, cyclic amines, unsaturated and aromatic amines as well as combinations thereof.

According to the invention, the plasma is produced by means of direct current (DC) or alternating current (AC), such as high or radio frequency (HF, RF), or microwaves (MW) at a low pressure, typically 0.1 Pa to 0.9 kPa. The present invention includes MW and RF plasmas at pressures of from 100 kPa to 500 kPa (normal pressure range).

In one embodiment of the process according to the invention, the plasma may be employed under inert gas, or with admixture of oxygen, hydrogen, water, hydrogen peroxide.

The ceramic materials forming the ceramic implant which can be used in the process according to the invention are selected, in particular, from the group consisting of leucite-containing or leucite-free oxide ceramic, feldspar ceramic.

According to the process of the invention, the organic phase can be formed from the organic compound selected from the group consisting of aliphatic amines, cyclic amines, unsaturated and aromatic amines as well as combinations thereof. The organic compounds may be, in particular, ethylene diamine, heptylamine, diaminopropane, (substituted) cyclopropylamines, diaminocyclohexanes, allylamine, dimethylformamide, nitrogen-containing heterocycles, such as azirines, pyrroles, pyridines, piperidines or pyrrolidines.

The present invention relates to a ceramic implant obtainable by the process according to the invention, and to a ceramic implant provided with at least partial coating by an organic phase. Said ceramic implant provided with at least partial coating by an organic phase has an organic phase with a thickness of from 1 nm to 10 µm. The coating is advantageously resistant to external mechanical stress, in particular, scratch-resistant. The coating is advantageously stable over the time frame of one year in its adhesiveness The present invention relates to an implant material having a scratch-resistant at least partial coating of an organic phase.

The present invention also relates to the use of said ceramic implant, especially in the orthopedic or dental field.

Plasmas suitable for creating an interface for functionalization in accordance with the process according to the invention include the following, in particular:

DC or HF plasmas (high frequency plasmas, including RF and microwave plasmas, 0 Hz to 10 GHz) in the low pressure range, i.e., from $10^{-1}$ Pa to 1 kPa, preferably around 10 Pa to 1 kPa, which are inductively and/or capacitively coupled. The plasmas may also be pulsed with duty cycles (the ratio of plasma on times to the duration of the period) of from $10^{-6}$ to 0.9, advantageously from 0.05 to 0.5, more suitably from 0.1 to 0.3. Normal pressure plasmas, such as barrier discharges, which have at least one dielectric barrier in the discharge space or are performed as coplanar discharge, may also be employed. The operating frequency of the applied (pulsed) alternating voltage is from 50 Hz to 500 kHz at voltages within a range of from 1 to 10 kV. Further, plasma jets are suitable. This term refers to plasma sources in which the plasma produced is blown by the current of working gas employed out of an opening into the surrounding space. They can be operated with pulsed direct voltage (1 to 15 kV at 10 to 25 kHz), MF (1 to 5 kV at 50 kHz) or microwaves (e.g. 1-10 GHz), as well as HF (e.g. 1-50 MHz). In this method, the plasma burns at an operating pressure of from 1 to $10^5$ Pa. The process according to the invention can employ plasmas in inert gases, but admixtures of oxygen, hydrogen, water, hydrogen peroxide are also possible. The plasmas may also burn within the latter as pure substances.

A correspondingly suitable plasma pretreatment yields a surface having a carbon content of <25% (XPS (X-ray photoelectron spectroscopy) measurement), preferably <20% (XPS measurement). The surface has chemically reactive oxygen-containing groups and free radicals, enabling a permanent bond to the nitrogen-containing functionalization.

In one embodiment, this plasma step can be directly combined with a second plasma step in one reactor without intermediate aeration. Thus, the corresponding plasma designed for a pretreatment is applied to the ceramic surface until the carbon content of typically 35-80% (XPS measurement), which corresponds to a C/Zr ratio of 1.5-20 in the case of YSZ (yttria-stabilized zirconia), has been reduced to values below 25%, preferably <20%, which corresponds to a C/Zr ratio of <1.3, preferably <0.8, in the case of YSZ (yttria-stabilized zirconia).

Without being limited to such explanation or to the hypothesis underlying the explanation, the process according to the invention for functionalization yields a firmly adhering, long-term water-stable functionalization of the surface, which includes introduced amino groups, in particular, and can cause adsorption of glycoproteins from the biological environment in which the implant is placed. The deposition of glycoproteins to the implant surface is one of the first steps of osseointegration. The process according to the invention enables functionalization, so that the roughness necessary for mechanical anchoring and other material properties important for the bond between the tissue and implant are retained.

In one embodiment of the process according to the invention, the plasma acts in the presence of nitrogen, ammonia and/or at least one nitrogen-containing, especially organic, compound on the surface of the ceramic implants.

According to the invention, at least one nitrogen-containing organic compound is selected from the group of aliphatic amines, cyclic amines, unsaturated amines and aromatic amines. Thus, in particular, the following substances may be mentioned in an exemplary way: ethylene diamine, heptylamine, diaminopropane, (substituted) cyclopropylamines, diaminocyclohexanes, allylamine, dimethylformamide, nitrogen-containing heterocycles, such as pyrroles.

Typically, the plasma is a microwave plasma, a DC or RF plasma (radio frequency, 0 Hz to 10 GHz) in the low pressure range, i.e., from 0.1 Pa to 1 kPa, preferably around 10 Pa to 1 kPa. The coupling of the energy may be effected inductively and/or capacitively. The plasma should advantageously be pulsed with duty cycles of from $10^{-6}$ to 0.9, advantageously from 0.05 to 0.5, more suitably from 0.1 to 0.3. Normal pressure plasmas, such as barrier discharges, which have at least one dielectric barrier in the discharge space or are performed as coplanar discharge, may also be employed. The operating frequency of the applied (pulsed) alternating voltage is from 50 Hz to 500 kHz at voltages within a range of from 1 to 10 kV. Further, atmospheric plasma jets are suitable. This term refers to plasma sources in which the plasma produced is blown by the working gas flow expending from the jet nozzle into the surrounding space. They can be operated with pulsed direct voltage (1 to 15 kV at 10 to 25 kHz), MF (1 to 5 kV at 50 kHz) or microwaves (1-10 GHz), as well as HF (1-50 MHz). In this method, the plasma burns at operating pressures of from 1 Pa to $10^5$ Pa. Preferably, anisothermic plasmas may be applied.

Upon contact with the implants prepared according to the invention, proteins adsorb and cells respond with a significantly improved initial attachment. In cell spreading, visibly intensified cell spreads as compared to untreated surfaces could be detected, also in the adhesion of the cells, which literally merge into the substrate topography.

This results in a significant shortening of the osseointegration time, and in addition, the mentioned functionalization is resistant to sterilization and long time stable.

In one embodiment, the ceramic implant according to the invention has an organic substrate on its surface, especially in a substantially uniform thickness of from 0.1 to 15 nm, preferably from 1 to 10 nm.

In a specific embodiment, the biologically active surface is applied in a high vacuum plasma reactor, i.e., to the implants that have already been morphologically structured. The high vacuum plasma reactors may be either microwave (MW, 2.45 GHz), radio frequency (RF, 13.56 MHz or 27.12 MHz) parallel plate reactors or inductively coupled plasmas (ICP reactors, 13.56 MHz or 27.12 MHz). The electric power is coupled, for example, at a low pressure (typically from 0.1-1 kPa), whereby a plasma is ignited and maintained for some time. The process sequence typically consists of two parts:

1. Exposure to a conditioning plasma in the presence of argon, oxygen, nitrogen, air, carbon tetrafluoride, or mixtures thereof for a sufficient time to activate the surface. The corresponding duration is known to the skilled person and is usually from $10^{-3}$ to $10^3$ s, preferably from 1 s to 100 s.
2a. A reactive plasma in which biologically active surfaces are produced by maintaining plasmas in aliphatic amines (such as ethylene diamine, heptylamine, diaminopropane), cyclic amines (such as cyclopropylamine, diaminocyclohexanes) or unsaturated amines (such as allylamine) (further examples, see above) with or without inert gas dilution (Ar, He, Xe) with or without admixing reactive gases ($NH_3$, $N_2$, air) with nitrogen-containing molecules, such as nitrogen and/or ammonia.
2b. Alternatively, aliphatic hydrocarbons (methane, ethane, propane, n-butane, isobutane), unsaturated hydrocarbons (ethylene, acetylene, propylene, butadiene), cyclic hydrocarbons (cyclopropane, cyclohexane) or aromatic hydrocarbons (benzene, toluene) may also be employed with or without inert gas dilution and with or without nitrogen-containing admixtures, such as ammonia ($NH_3$), hydrogen or amines. Thus, carbon surfaces may also be produced and subsequently activated with nitrogen-containing plasmas ($N_2$, $NH_3$, $H_2$ or amines).

In another embodiment of the process according to the invention, the implants with the ceramic surface were attached to a motor by means of a receptor means, and rotated. A plasma jet operated in argon (1.1 MHz) is scanned over the implants with or without admixture of oxygen in such a way that the entire length is activated. Any admixing of oxygen is stopped, and thereafter, the conditioning is effected by admixing aliphatic amines (e.g., ethylene diamine, heptylamine, diaminopropane), cyclic amines (e.g., cyclopropylamine, diaminocyclohexanes), or unsaturated amines (e.g., allylamine).

The invention is further illustrated by means of the following examples.

EXAMPLE 1

The biologically active surface is applied in a vacuum plasma reactor to the implants that have already been morphologically structured. The vacuum plasma reactor V55G (Plasma-finish, Schwedt, Germany) is made of aluminum and has dimensions of 40×45×34 cm³ (width×depth×height). The plasma is ignited by means of a microwave plasma source (microwave, MW, 2.45 GHz), which couples its power into the reactor through a microwave parabolic mirror. The implants are kept in a rotation means that causes rotation of the implants in the reactor both at 8 revolutions/min and at 120 revolutions/min about their own axis.

For conditioning the implant surfaces, the reactor is first evacuated to 6 Pa, followed by introducing an oxygen/argon mixture with flow rates of 100 sccm $O_2$ and 25 sccm Ar (sccm=standard cubic centimeters per minute), which is stabilized at 0.5 mbar within one minute. With a microwave power of 500 W, a continuous (cw) plasma is ignited for one minute at the mentioned parameters (50 Pa, 100 sccm $O_2$, and 25 sccm Ar). Subsequently, the mixture of gases is pumped off (6 Pa). The samples remain under vacuum.

On the implants, a surface has formed that lead to a very strong adhesion of the subsequent biologically active finishing of the surface.

For biologically active conditioning, a mixture of argon (50 sccm) and allylamine (1.5 ml/15 min, i.e., 100 µl of liquid/min) is adjusted. After a period of one minute, the MW plasma (2.54 GHz) with a power of 500 W is ignited and pulsed (300 ms on, 1700 ms off) for 240 s (24 s effectively). Thereafter, the mixture of gases is pumped off, and the reactor is aerated with nitrogen.

EXAMPLE 2

Two types of ceramic surfaces differing in their roughness were applied. The root-mean-squared-roughnesses $R_q$ are 294±3 nm and 747±42 nm determined with the profiler Dektak 3ST (Veeco, St. Barbara, USA, radius of the standard diamond stylus 2.5 µm, stylus force 30 mg, scan length 500 µm; 100 measurements/sample a'500 µm length at 3 sample of one charge). At first, the surfaces were exposed to a Ar/$O_2$-conditioning plasma (micro wave, 2.45 GHz, 500 W, 50 Pa, 60 s) followed by the treatment with the reactive plasma (microwave, 2.45 GHz, 500 W, 50 Pa, 144 s effective) in the presence of the precursor allylamine for generation of a bioactive surface. By XPS surface analyses (results shown in FIGS. 1A und B) elevated nitrogen content was detected expressed as N/C-ratio between 25 and 30%. The density of the amino groups $NH_2$/C on the surface was 2-3%.

FIG. 2A-D show the behaviour of cells when contacted with the surface treated according to example 2. For morphological cell observations human osteoblast-like cells (cell line MG-63, ATCC, CRL-1427, LGC Promochem, Wesel, Germany) were cultured in Dulbecco's modified Eagle's medium, serum-free, 1% gentamicin from Ratiopharm GmbH, Ulm, Germany at 37° C. in a humidified atmosphere with 5% $CO_2$ on the untreated as well as modified ceramic surfaces for 24 h, fixed with 4% glutaraldehyde (1 h), dehydrated through a graded series of acetone, dried in a critical point dryer (K 850, EMITECH, Taunusstein, Germany), sputtered with a coater (SCD 004, BAL-TEC, Balzers, Lichtenstein) and observed in the scanning electron microscope (SEM, DSM 960A, Carl Zeiss, Oberkochen, Germany).

EXAMPLE 3

Figures 3A, 3B:
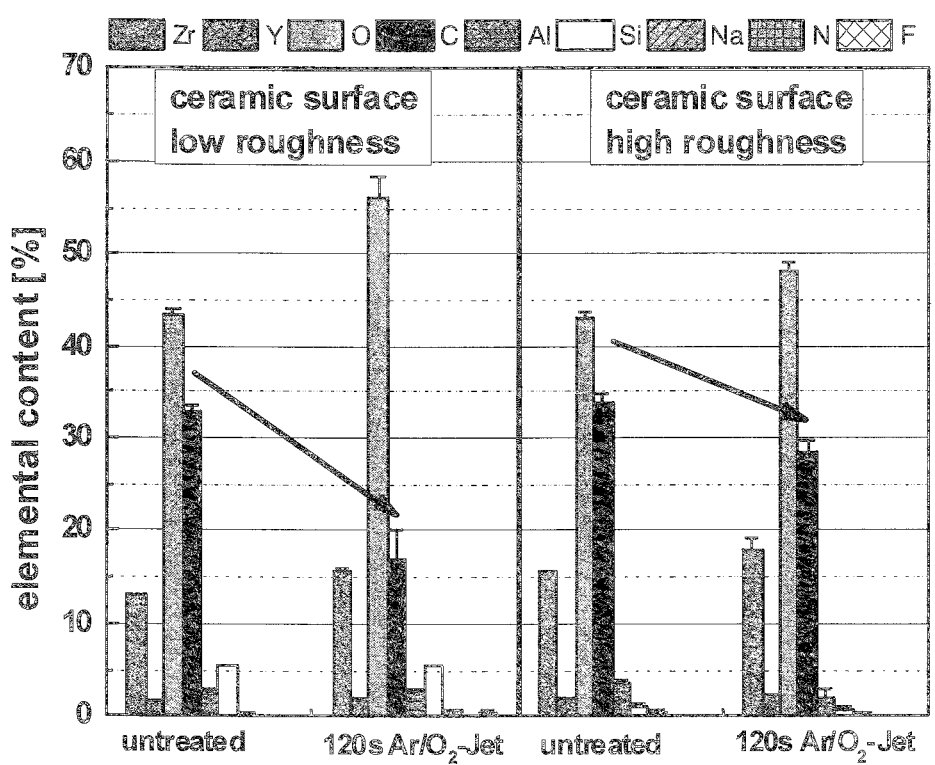
FIG. 3A is a plot of results of an XPS analysis of a ceramic surfaces of low roughness.
FIG. 3B is a plot of results of an XPS analysis of a ceramic surfaces of high roughness.
Figure 4A:
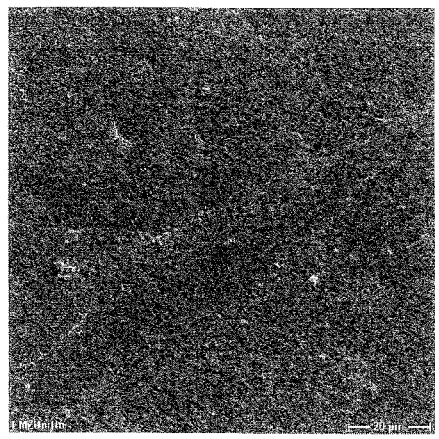
FIG. 4A is a scanning electron micrograph image of an untreated ceramic surface having low roughness.
Figure 4B:
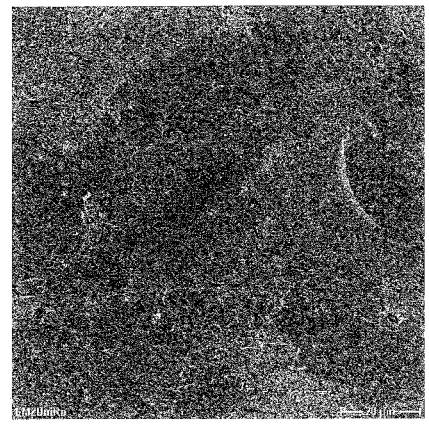
FIG. 4B is a scanning electron micrograph image of a treated ceramic surface having low roughness.
Figure 4C:
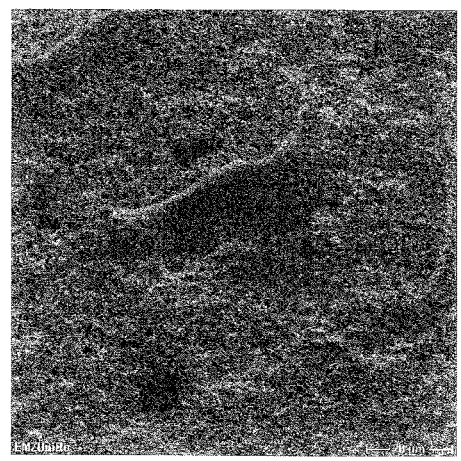
FIG. 4C is a scanning electron micrograph image of an untreated ceramic surface having high roughness.
Figure 4D:
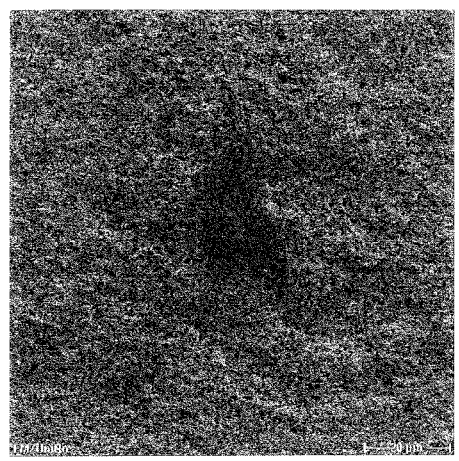
FIG. 4D is a scanning electron micrograph image of an treated ceramic surface having high roughness.

Two types of ceramic surfaces differing in their roughness were applied. The root-mean-squared-roughnesses $R_q$ are 294±3 nm and 747±42 nm determined with the profiler Dektak 3ST (Veeco, St. Barbara, USA, radius of the standard diamond stylus 2.5 µm, stylus force 30 mg, scan length 500 µm; 100 measurements/sample a '500 µm at 3 sample of one charge). The surfaces were exposed to an Ar/$O_2$ normal pressure plasma (HF, 1 MHz, 10 W, 100 kPa, 120 s) and a bioactive surface was generated. A C/Zr-ratio of <1.3 was found by XPS analyses. The results are shown in FIGS. 3A und B.

FIG. 4A-D show the behaviour of cells when contacted with the surface treated according to example 3. The osteoblast cultivation on the ceramic samples, the preparation and the finally observation using SEM is already described above (FIG. 2).

The invention claimed is:

1. A process for manufacturing a ceramic implant with a surface which forms an initial and a permanent bonding to bone cell tissues, the surface providing improved osseointegration, the process comprising
   a pretreatment of the ceramic implant with the surface wherein said surface of the ceramic implant is exposed to a conditioning plasma produced by process selected from the group consisting of direct current (DC), alternating current (AC), high frequency (HF), radio frequency (RF), and microwaves (MW) at a low pressure, followed by
   a treatment with a reactive plasma in which an organic compound is added to the plasma for an at least partial application of an organic phase to said surface wherein the organic compound is selected from the group consisting of aliphatic amines, cyclic amines, unsaturated amines, aromatic amines and combinations thereof.

2. The process according to claim 1, wherein MW and RF plasmas are produced at pressures of from 100 kPa to 500 kPa.

3. The process according to claim 1 wherein said plasma is employed under inert gas, or with admixture of oxygen, hydrogen, water, hydrogen peroxide.

4. The process according to claim 1, wherein said ceramic implant comprises materials selected from the group consisting of leucite-containing oxide ceramic, leucite-free oxide ceramic, and feldspar ceramic.

5. The process according to at least one of claim 1, wherein said organic compounds are chosen from the group consisting of ethylene diamine, heptylamine, diaminopropane, cyclopropylamines, unsubstituted cyclopropylamines, diaminocyclohexanes, allylamine, dimethylformamide, nitrogen-containing heterocycles, azirines, pyrroles, pyridines, piperidines, and pyrrolidines.

6. A ceramic implant provided with an organic phase obtainable by the process according to claim 1.

7. The ceramic implant according to claim 6 provided with an at least partial coating by an organic phase having a thickness of from 1 nm to 10 µm.

8. The ceramic implant according to claim 6 having a density of amino groups on its surface of 1-8% $NH_2$/C, determined by XPS measurements.

9. The material according to claim 6 provided with an at least partial coating by an organic phase that is resistant to external mechanical stress.

10. A method of use of the ceramic implant according to claim 6 comprising placing the implant in a patient.

11. The method of claim 10 wherein the implant is a dental implant or an orthopedic implant.

* * * * *